United States Patent [19]

Ratajczyk et al.

[11] Patent Number: 5,580,989

[45] Date of Patent: Dec. 3, 1996

[54] PROCESS FOR THE PREPARATION OF N-4-[(SUBSTITUTED PHENYL)ALKYLHETEROCYCLIC]-N-HYDROXYUREA COMPOUNDS

[75] Inventors: James D. Ratajczyk, Waukegan; Juliette K. Busse, Winthrop Harbor; Sanjay R. Chemburkar, Gurnee; Daniel A. Dickman, Grayslake; Yi-Yin Ku, Buffalo Grove; Hemantkumar H. Patel, Waukegan; Ramesh R. Patel, Chicago; David P. Sawick, Wildwood; John N. Starr, Grayslake; Bhadra Shelat, Lake Forest, all of Ill.; Harry O. Spiwek, Kenosha, Wis.

[73] Assignee: Abbott Laboratories, Abbott Park, Ill.

[21] Appl. No.: 472,448

[22] Filed: Jun. 7, 1995

Related U.S. Application Data

[63] Continuation-in-part of Ser. No. 147,616, Nov. 15, 1993, abandoned.

[51] Int. Cl.$^6$ .................. C07D 333/22; C07D 307/36
[52] U.S. Cl. ........................ 549/77; 549/496
[58] Field of Search ........................ 549/77, 496

[56] References Cited

U.S. PATENT DOCUMENTS 5,288,751  2/1994  Brooks et al. ................ 514/438

FOREIGN PATENT DOCUMENTS 9512589  5/1995  WIPO.
9530671  11/1995  WIPO.

OTHER PUBLICATIONS

Sonogashira et al., Tetrahedron Letters, (50), 4467, 1975.
March, J., "Adv. Org. Chem: Reactions, Mechanisms, & Structure" 3rd Ed, John Wiley & Sons, NY, 1985.
Carey et al, "Adv. Org. Chem.: Part B: Reactions & Structure," 3rd Ed., Plenum Press, NY 1990.
Brooks et al., J. Med. Chem., 38(24), 4768–75, 1995.

Primary Examiner—José G. Dees
Assistant Examiner—Mary C. Cebulak
Attorney, Agent, or Firm—Mona Anand; Jerry F. Janssen

[57] ABSTRACT

A process for preparing a compound of the structure I

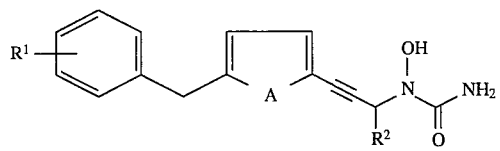

where A is oxygen and sulfur and $R^1$ is selected from the group consisting of hydrogen, halogen, alkyl of one to six carbon atoms, alkoxy of one to six carbon atoms, and trifluoromethyl, and $R^2$ is alkyl of one to four carbon atoms, comprising coupling a compound of formula II:

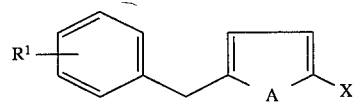

where X is bromine or iodine, with an N-hydroxyurea compound of formula III:

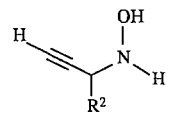

in the presence of a palladium catalyst followed by reaction of the product thus formed with an alkali metal isocyante.

The compounds of formula I are inhibitors of the enzyme 5-lipoxygenase and are thus useful as therapeutic agents for the treatment of allergic and inflammatory disease conditions.

14 Claims, No Drawings

PROCESS FOR THE PREPARATION OF N-4-[(SUBSTITUTED PHENYL)ALKYLHETEROCYCLIC]-N-HYDROXYUREA COMPOUNDS

CROSS-REFERENCE TO RELATED APPLICATIONS

This application is a continuation-in-part of application Ser. No. 08/147,616 filed Nov. 15, 1993, now abandoned.

TECHNICAL FIELD

The present invention relates to chemical synthetic processes. More particularly, the present invention concerns a process for the preparation of a class of N-4-[(substituted phenyl)alkylthienyl]-, and N-4-[(substituted phenyl)alkylfuryl]but-3-yn-2-yl]-N-hydroxyurea compounds.

BACKGROUND OF THE INVENTION

Compounds of Structure I

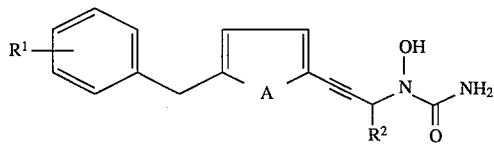

where A is oxygen or sulfur and $R^1$ is alkyl, halogen, alkoxy, or trifluoromethyl, and $R^2$ is hydrogen or lower alkyl, have been found to be effective inhibitors of the enzyme 5-lipoxygenase. This enzyme is involved in the conversion in the human body of arachidonic acid to the leukotrienes which have been implicated in inflammatory disease conditions. The compounds are thus useful therapeutic agents in the treatment of asthma, arthritis, inflammatory bowel syndrome, and similar conditions.

SUMMARY OF THE INVENTION

In its broadest aspect, the present invention provides an efficient and cost-effective process for the preparation of a compound having the structure:

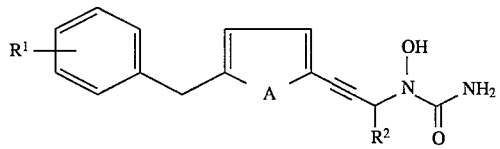

where A is oxygen or sulfur, $R^1$ is selected from hydrogen, halogen, alkyl of one to six carbon atoms, alkoxy of one to six carbon atoms, and trifluoromethyl and $R^2$ is hydrogen or alkyl of one to four carbon atoms.

The process comprises coupling a compound of formula II:

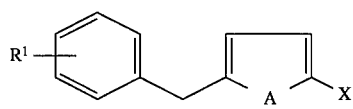

where $R^1$ and A are as defined above and X is bromine or iodine, with a compound of formula III:

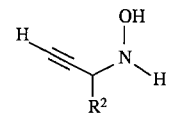

where $R^2$ is as defined above, and subsequently reacting the product or a salt thereof thus formed, with an alkali metal isocyanate.

The present invention also encompasses processes for making the intermediates II and III for the coupling reaction described above.

DETAILED DESCRIPTION

As used throughout this specification and the appended claims, various terms and phrases have the meanings ascribed to them as follows.

By "alkyl" is meant a monovalent group which can be thought of as deriving from a straight or branched saturated hydrocarbon by the removal of a single hydrogen atom.

"Alkoxy" denotes an alkyl group as defined above, attached to the parent molecular moiety through an oxygen atom.

In general, the process of the present invention involves three distinct phases, including 1) the synthesis of the so-called "lefthand" (substituted phenylalkyl)thienyl- or-furyl halide portion; II, 2) the synthesis of the so-called "righthand" N-hydroxylamine portion. III, and 3) coupling of the two precursor halves, II and III, and reaction of the product thus formed with an alkali metal isocyanate to form the final product, I.

These parts of the total synthesis are termed "phases" of the process rather than steps, since it is to be understood that the preparation of the righthand and lefthand portions of the molecule can be carried out in any order and are thus not "steps" of the process in the usual sense of the term. The final step of joining or coupling the two precursors molecules must, of course, follow their prior synthesis.

Preferred Method of Synthesizing the "Lefthand" Precursor, II

The lefthand (substituted phenyl)alkylfuran or (substituted phenyl)alkylthienyl precursor is preferably synthesized by the reaction sequence depicted in Reaction Scheme 1. This process, from the initial preparation of the Grignard reagent intermediate, 2, to the final coupling step leading to the formation of the "lefthand" precursor, 5, can be conveniently carrier out in a single vessel in yields typically exceeding 80%.

Reaction Scheme 1

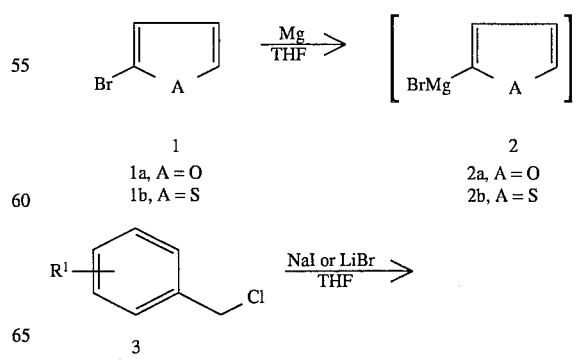

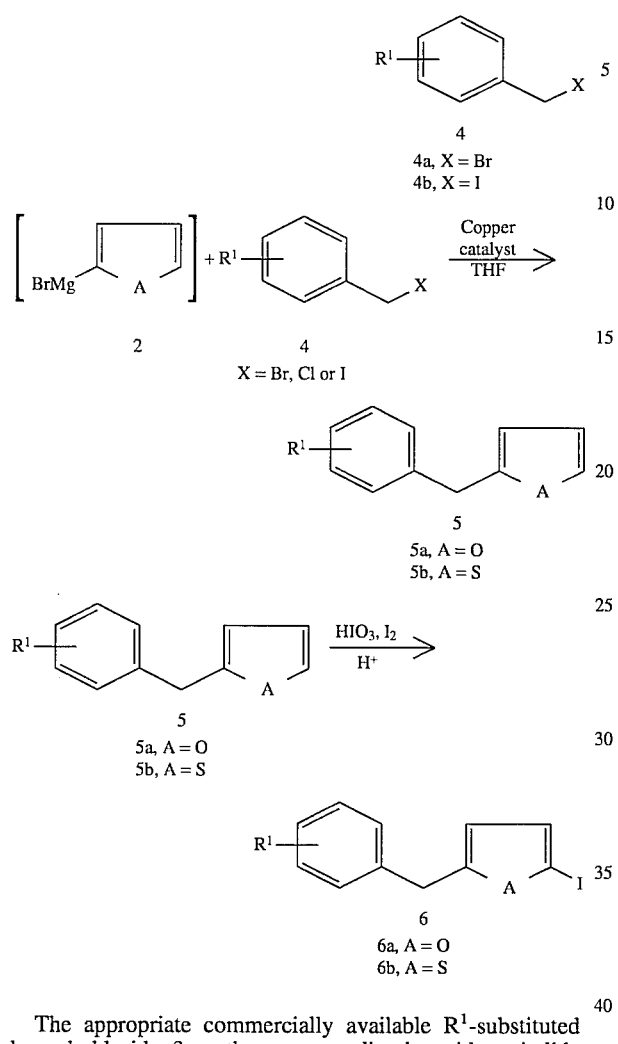

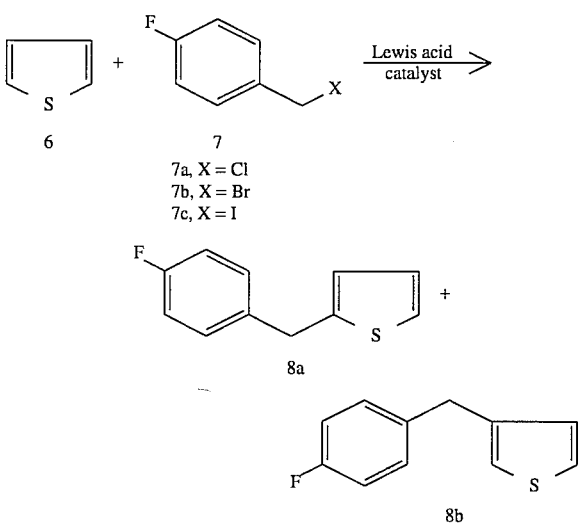

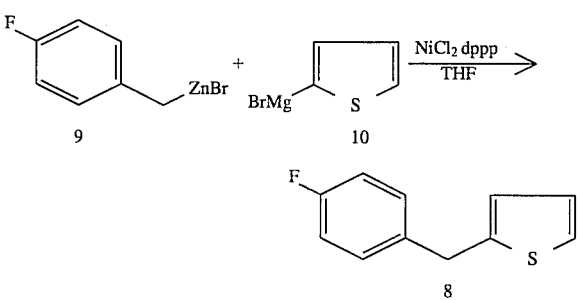

The appropriate commercially available $R^1$-substituted benzyl chloride, 3, or the corresponding bromide or iodide (obtained by conversion of the $R^1$-substituted benzyl chloride by reaction with lithium bromide or sodium iodide in a suitable polar aprotic organic solvent such as tetrahydrofuran) is reacted with the furyl or thienyl Grignard reagent, prepared as described below. Commercially available 2-bromofuran, 1a, or 2-bromothiophene, 1b, is converted under typical Grignard reaction conditions to the corresponding Grignard reagent, 2a or 2b.

The $R^1$-substituted benzyl chloride, 3, bromide, 4a, or iodide, 4b, is reacted with the thienyl or furyl Grignard reagent in tetrahydrofuran in the presence of a copper catalyst selected from CuCN, CuCl, Cu[CN]$_2$Li$_2$Cl$_2$ and Li$_2$CuCl$_4$. The preferred catalyst is a copper(I) catalyst. which acts as a coupling catalyst to yield the desired $R^1$-substituted benzylfuran, 5a, or benzylthiophene, 5b. The $R^1$-substituted benzylfuran, 5a, or benzylthiophene, 5b, is finally converted to the 5-($R^1$-substituted phenyl)-2-iodo- or bromofuran, 6a, or thiophene, 6b, by reaction with iodine in the presence of HIO$_3$ or reaction with bromine. The iodination reaction is carried out typically at temperatures ranging between ambient and about 50° C., preferably at about 30° C. to about 40° C. for periods ranging between about 5 to about 24 hours. The solvent system for this step comprises acetic acid/ethyl acetate/sulfuric acid. The bromination is carried out under conditions typical for bromination of aromatic systems.

Alternative Methods of Synthesizing the "Lefthand" Precursor

Alternative 1—Friedel-Crafts alkylation (Illustrated with thiophene and 4-fluorobenzyl chloride, bromide, or iodide)

Friedel-Crafts alkylation of thiophene with 4-fluorobenzyl chloride, 4-fluorobenzyl bromide or 4-fluorobenzyl iodide) in the presence of a Lewis acid catalyst (AlCl$_3$, ZnCl$_2$, or EPZ10) were found to produce a mixture of 2- and 3-alkylation products in roughly equal amounts. The resulting reduced yield of the desired product and the separation of the product mixture makes this process less desirable.

Alternative 2—Transition metal catalyzed coupling of Grignard reagents (illustrated with 2-bromothiophene and 4-fluorobenzyl bromide)

The Nickel catalyzed coupling reaction of 4-fluorobenzylzinc bromide and the Grignard reagent derived from 2-bromothiophene failed to produce 2-(4-fluorobenzyl)thiophene in reasonable yield. Although several different methods for activating the zinc were used to prepare the organozinc reagent, all of them failed to improve the yield.

Alternative 3—Transition metal Catalyzed coupling of a substituted benzyl halide with a Grignard reagent (Illustrated with 4-fluorobenzyl chloride, bromide or iodide and the Grignard reagent derived from 2-bromothiophene)

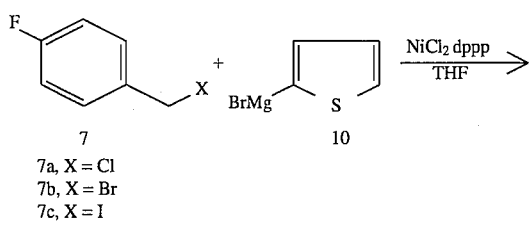

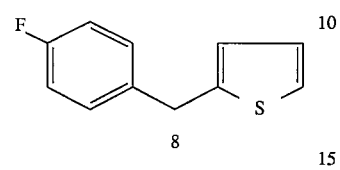

The Nickel catalyzed coupling reaction of the Grignard reagent derived from 2-bromothiophene with 4-fluorobenzyl chloride, 4-fluorobenzyl bromide or 4-fluorobenzyl iodide was found to work well in small scale (10 mmol), but when attempts were made to scale the reaction up (100 mmol), numerous undesired by-products were produced.

Alternative 4—"Kumada" coupling of the Grignard reagent derived from a substituted benzyl halide with 2-bromothiophene (Illustrated with the Grignard reagent derived from 4-fluorobenzyl chloride and 2-bromothiophene)

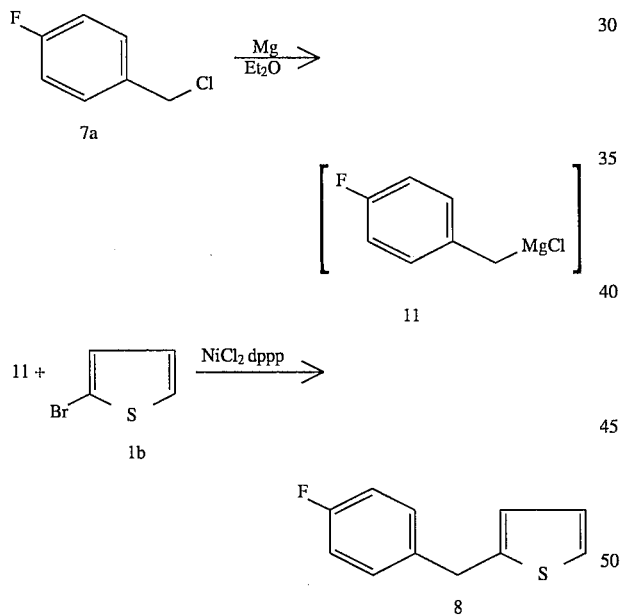

Kumada, Tetrahedron, 38:3347 (1982) has described the production of 2-benzyl thiophene by the coupling reaction illustrated above for the 4-fluorobenzyl starting material. The process has the disadvantage that the reaction is carded out in diethyl ether, which is highly flammable.

Alternative 5—A two step Grignard process:

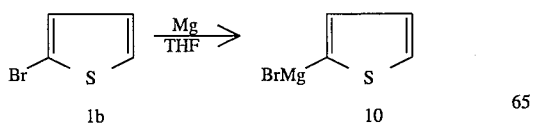

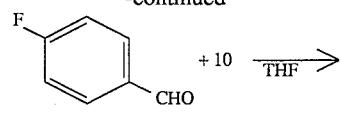

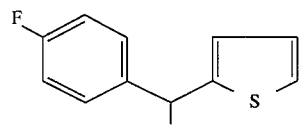

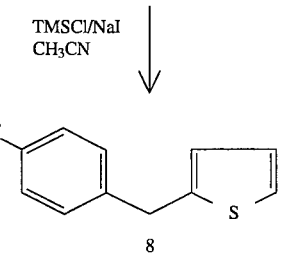

This process involves an addition of an aldehyde to a thiophene Grignard followed by deoxygenation of the resulting secondary alcohol. The quality of the product is not good enough for use in the next step without purification by vacuum distillation.

Alternative 6—Alkylation of furyl- or thienyllithium (Illustrated with 4-fluorobenzyl bromide and 2-lithiothiophene)

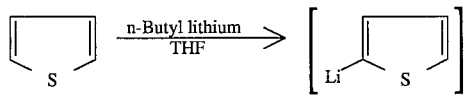

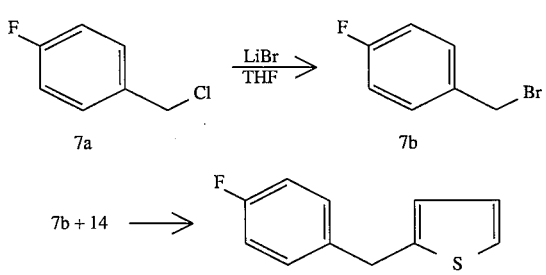

This process, while effective in producing the desired intermediate, 8, suffers from the disadvantage that it requires the use of n-butyl lithium. The hazards associated with its use on a large scale preclude this method from choice for commercial-scale production of the intermediate, 8.

Preferred Method of Synthesizing the "Righthand" Alkynic N-Hydroxylamine, III

The righthand precursor portion of the end-product of the process of this invention is an acetylenic-N-hydroxylamine compound of structure III:

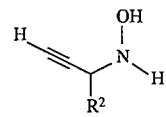

The substituent group $R^2$ may be hydrogen or lower alkyl, preferably methyl. When $R^2$ is other than hydrogen, there is a chiral center in compounds of structure III at the carbon atom which bears the $R^2$ substituent. The present invention contemplates process for making both enantiomers of III, as well as mixtures of the two including the racemic mixture. In addition, the present invention contemplates processes for making both enantiomers of the final products of structure I above. The latter process is a natural consequence of the former; that is, once the desired enantiomer or enantiomeric mixture of III is produced, coupling of that material with an intermediate of structure II above results in the desired enantiomeric form of I or enantiomeric mixture, since the coupling reaction does not affect the chiral center.

In order to achieve the desired chirality in the end product, it is necessary that the coupling step be perfomed after the step in which the chiral acetylenic hydroxylamine is produced by displacement of the leaving group on the derivatized butynol with hydroxylamine. If the butynol (or a derivative thereof) is first coupled to the "lefthand" piece prior to conversion to a hydroxylamine, chiral integrity of the end product cannot be assured.

The preferred method of synthesizing the righthand piece is depicted in Reaction Scheme 2 where, for the sake of illustration, the reaction sequence employs the preferred starting material, S-3-butyn-2-ol (i.e. $R^2$=methyl). It is to be understood, however, that the same reaction sequence can be employed with other starting alcohols corresponding to $R^2$ being alkyl of two to four carbon atoms, or with the non-chiral alcohol, propynol ($R^2$=hydrogen).

Reaction Scheme 2

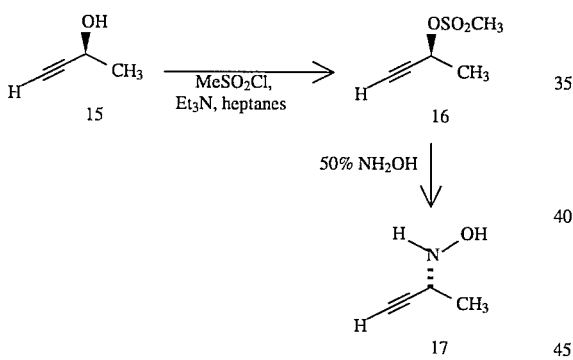

Referring to Reaction Sequence 2, the preferred S-enantiomer of 3-butynol, 15, is converted to the corresponding methanesulfonic acid ester ("mesylate"), 16, by conventional means. The reaction is typically carried by reacting methanesulfonyl chloride with the alcohol at lower temperatures, generally about 0° C. to about room temperature, preferably about 0° C. to about 10° C., in an inert organic solvent. An acid scavenger such as a tertiary amine (e.g. triethylamine) is employed in the reaction mixture. Reaction times range from about one-half to six hours, typically from about one to two hours for substantially complete conversion of the alcohol to the methanesulfonate ("mesylate") 16.

Although the mesylate is preferred, other butynol derivatives e.g. the p-toluenesulfonate ("tosylate"), and the triflate may also be employed in this step of the process. The tosylate and triflate of 3-butynol were also prepared and their reaction with aqueous hydroxylamine proceeded smoothly.

In the next step, the mesylate, 16, is reacted with 50% hydroxylamine, resulting in a typical Sn2 nucleophilic displacement of the methansulfonate leaving group to produce the inverted hydroxylamine, 17. The displacement reaction can be carried out in a hydrocarbon solvent such as hexanes, heptanes, octanes and the like, or in a more polar solvent such as methanol, ethanol, isopropanol or THF as the reaction solvent resulting in overall production of compound 17 in yields uniformly exceeding 85%.

This reaction appears to produce almost complete inversion at the chiral center. Thus, if the desired hydroxylamine is the preferred R-enantiomer, the starting alcohol of choice is the S-3-buty-2-nol. For the production of the S-hydroxylamine, the desired starting material is the R-3-butyn-2-ol and, of course, racemic alcohol produces the racemic hydroxylamine.

Racemic 3-butynol and the R- and S-enantiomeric forms are commercially available or may be made by various methods including resolution by conversion to an ester followed by enzymatic hydrolysis to produce a mixture of one enantiomer of the alcohol and the ester of the other followed by conventional physical separation. Alternatively, the racemic alcohol may be preferentially esterified by enzyme catalysis to produce a mixture of one enantiomer of the alcohol and an ester of the other, followed by physical separation.

In the process described above the starting alcohol, S-3-butyn-2-ol, is preferably converted to a derivative in which the alcohol oxygen atom is derivatized by a methanesulfornate leaving group. Other leaving groups which may be used include the p-toluenesulfonate ("tosylate"), p-chlorophenylsulfonate, and trifluoromethylsulfonate ("triflate").

The leaving group on the 3-butynol is displaced by a nucleophile which effects the replacement of the alcohol oxygen atom with a nitrogen, from which an N-hydroxylamine or urea ultimately derives. Suitable nucleophiles include hydroxylamine, hydroxylamine hydrochloride, and reagents of the structure

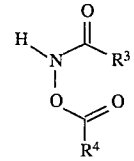

in which $R^3$ and $R^4$ are independently lower alkoxy, phenoxy or substituted phenoxy. The synthesis of reagents of this type is described by Stewart and Brooks in *J. Org. Chem.*, 57(18): 5020–5023 (1992).

Displacement of the leaving group on the S-3-butyn-2-ol by the nucleophile is generally carried out in the presence of a base such as an alkali metal carbonate or bicarbonate such as potassium or sodium carbonate or bicarbonate, alkali metal alkoxides such as potassium t-butoxide, alkali metal hydrides such as sodium hydride, n-butyl lithium, pyridine, 2,6-lutidine, and the like.

Suitable solvents include tetrahydrofuran, dimethylformamide, dimethylsulfoxide, methylene chloride, pyridine, acetonitrile and the like.

Preferred Method of Coupling II and III to Form I:

In the last stage of the method of this invention, the so-called "lefthand" piece, II, is coupled to the righthand piece, III. The coupling process is carried out in any one of a number of suitable solvents selected from tetrahydrofuran, dimethylformamide, acetonitrile, ethyl acetate, dichloromethane, or a biphasic system comprising isopropyl acetate and water.

The coupling reaction is generally carried out in the presence of a base such as triethylamine, diethylamine, diisopropylamine, isopropylamine, potassium or sodium carbonate, or sodium acetate.

Either the substituted 2-bromo- or 2-iodofuran or -thiophene, can be coupled with the righthand N-hydroxylamine piece, III, although the substituted 2-iodothiophene or 2-iodofuran is preferred since the corresponding 2-bromo-compounds produced somewhat lower yields and required longer reaction times.

The coupling is catalyzed by a palladium catalyst which may take the form of $PdCl_2$, $PdOAc_2$, $(CH_3CN)_2PdCl_2$, $Pd(PPh_3)_4$, and polymer supported Pd(0) with $(CH_3CN)_2PdCl_2$ being the preferred catalyst.

In a particularly preferred alternative of the process of the present invention, the crude coupling product is converted to its sulfate salt and the salt is purified by washing with organic solvents prior to reaction of the coupling product with an alkali metal isocyanate to form the final product. The sulfate salt is formed by contacting the crude coupling product with dilute (about 10–25%) aqueous sulfuric acid. Organic solvents suitable for the washing step are isopropyl acetate, methyl tert-butyl ether, ethyl acetate and the like.

EXAMPLE 1

Preparation of of 2-(4-fluorobenzyl)thiophene

To a suspension of Mg turnings (3 g, 0.123 mol) in THF (40 ml) was added a small amount of solid $I_2$ (20 mg). The mixture was heated to reflux under nitrogen. To the mixture was then added a small reaction-initiating amount (5 ml) of a solution of 19.6 g of 2-bromothiophene in 40 ml of THF. After the iodine color disappeared, the remainder of the 2-bromothiophene solution was added dropwise at a rate to maintainin reflux. After the addition, the mixture was heated under reflux for 2 hours, then was cooled to room temperature. To this mixture was added 0.3 g of CuCl catalyst followed by the dropwise addition of 4-fluorobenzyl chloride (14.4 g), again at a rate to maintain reflux. The mixture was stirred at room temperature for 2 h. After this period, saturated NH4Cl solution (100 ml) was added and the mixture was stirred for 30 min., the organic layer was separated and washed with 10% sodium thiosulfate solution (50 ml), followed by distilled water (100 ml). The organic layer was then dried over $MgSO_4$ and concentrated to give 19 g of 2-(4-fluorobenzyl)thiophene as an oil. Purification was achieved by vacuum distillation (110° C., 5 mmHg).

EXAMPLE 2

Preparation of 5-(4-Fluorobenzyl)-2-iodothiophene

A mixture of 2-(4-fluorobenzyl)thiophene (8.4 g, 43.7 mmol), $HIO_3$ (1.86 g, 10.6 mmol), $I_2$ (4.86 g, 19.2 mmol), ethyl acetate (66 ml), acetic acid (7.7 ml) and conc. $H_2SO_4$ (0.79 ml) was heated at 35° C. overnight (GC-MS showed that all the starting material is converted to 5-(4-fluorobenzyl)-2-iodothiophene). To the reaction mixture was added brine solution (33 ml), the organic layer was separated and washed with sodium hydroxide/sodium thiosulfate solution (33 ml) (prepared from 2.3 g of NaOH, 3.3 g of $Na_2S_2O_3$ in 27 ml of $H_2O$), followed by 10% of $NaHCO_3$ solution (33 ml). The organic layer was concentrated to yield 13.9 g of 5-(4-fluorophenyl)-2-iodothiophene.

EXAMPLE 3

Synthesis of R-(+)-N-(3-butyn-2-yl)-N-hydroxylamine

A 1 L three-neck flask equipped with mechanical stirrer, reflux condensor and a dropping funnel was charged with S-3-butyn-2-ol (35.0 g, 0.5 mol) in heptanes (500 mL). The mixture was cooled to 5° C. and triethylamine (65.5 g, 90 mL, 0.65 mol) was added. Methanesulfonyl chloride (78.5 g, 46 mL, 0.6 mol) was added dropwise keeping the temperature below 10° C. The reaction mixture was stirred at 5° C.–10° C. for 1.5 hours. To this reaction mixture was added 50% aqueous $NH_2OH$ (300 mL, 5 mol). The mixture was stirred at 23° C. for 8 hours. The heptane layer was removed and the aqueous layer extracted with ethyl acetate (5×300 mL). The combined ethyl acetate extracts were mixed with 60 g of acetone and the mixture was concentrated. The crude hydroxylamine product was used without further purification in the next step of the process.

EXAMPLE 4

Preparation of N-(4-(5-(4-Fluorobenzyl)thien-2-yl)but-3-yn-2-yl)-N-hydroxyurea

A 500 mL three-neck flask equipped with mechanical stirrer and nitrogen inlet was charged with 5-(4-fluorobenzyl)-2-iodothiophene (31.8 g, 0.1 mol), R-(+)-N-(3-butyn-2-yl)-N-hydroxylamine (8.5 g, 0.1 mol), $(CH_3CN)_2PdCl_2$ (129 mg, 0.5 mmol), $PPh_3$ (262 mg, 1.0 mmol), CuI (190 mg, 1.0 mmol) and tetrahydrofuran (200 mL). To this mixture, diisopropylamine (15.1 g) was added and it was stirred at 30° C. for 2.5 hours. A solution of ammonium hydroxide (20%, 150 mL) was added and the mixture was stirred for 30 min. The aqueous phase was separated and discarded and the organic layer was cooled to about 0° C. To this was added a solution of 24 g of sulfuric acid in 210 ml of water. The resulting precipitate was collected by filtration and washed with 200 g of isopropyl acetate. The solid cake was taken up in 200 ml of ethyl acetate and the resulting mixture cooled to about 5° C. The cooled solution was treated with a solution of 16 g of KOCN in 100 ml of water and stirred for about one hour. Ammonium hydroxide solution (30 g) was added and the mixture stirred for about fifteen minutes. The lower aqueous layer was separated and discarded and the organic layer was treated with activated carbon (3.2 g) and filtered through a silica bed. The filtrate was concentrated and heptanes (192 g) were added to cause precipitation. The solid product was collected by filtration and dried to yield N-(4-(5-(4-fluorobenzyl)thien-2-yl)but-3-yn-2-yl)-N-hydroxyurea (18 g) as a white solid.

While there have been described what are believed to be the preferred embodiments of the process of the present invention, it will be apparent to one of ordinary skill in the art that various modifications may be made in the described process without departing from the scope of the invention as defined by the appended claims.

We claim:

1. A process for preparing a compound of the structure I

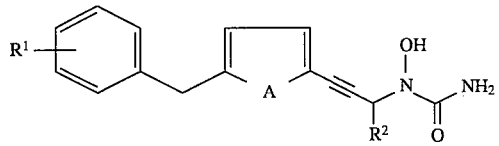

where
   A is selected from oxygen and sulfur;
   $R^1$ is selected from the group consisting of hydrogen, halogen,
alkyl of one to six carbon atoms,
alkoxy of one to six carbon atoms, and
trifluoromethyl; and
R² is hydrogen or alkyl of one to four carbon atoms;
comprising coupling a compound of formula II:

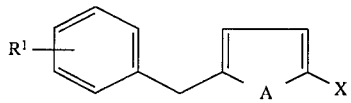

II where R¹ and A are as defined above and X is bromine or iodine,
with a hydroxylamine compound of formula III:

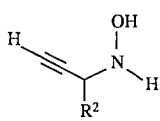

III where R² is as defined above, followed by reaction with an alkali metal isocyanate.

2. The process of claim 1 wherein X is iodine.
3. The process of claim 1 wherein A is sulfur.
4. The process of claim 1 wherein A is oxygen.
5. The process of claim 1 wherein R¹ is halogen.
6. The process of claim 4 wherein R¹ is fluorine.
7. The process of claim 1 wherein said coupling is carried out in the presence of a palladium catalyst.
8. The process of claim 7 wherein said palladium catalyst is selected from the group consisting of PdCl₂, Pd(OAc)₂, (CH₃CN)₂PdCl₂, and Pd(PPh₃)₄.
9. The process of claim 1 further comprising the steps of preparing said compound II in a one vessel reaction comprising the steps of
   a) first reacting a compound of the formula

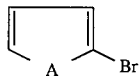

with magnesium to form the corresponding Grignard reagent intermediate, and
   b) subsequently reacting said Grignard reagent intermediate with a compound of the formula

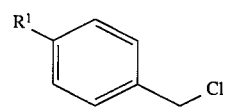

in a polar, aprotic organic solvent in the presence of a copper catalyst.

10. The process of claim 9 wherein said copper catalyst is selected from the group consisting of CuCN, CuCl, Cu[CN]₂.2LiCl and CuCl₂.2LiCl.
11. The process of claim 9 wherein A is sulfur and R¹ is fluorine.
12. The process of claim 1 further comprising the steps of (a) converting the product of the coupling reaction of compound II and compound III to a salt, followed by (b) purification of said salt prior to reaction with an alkali metal isocyanate.
13. A process for preparing a compound of the structure

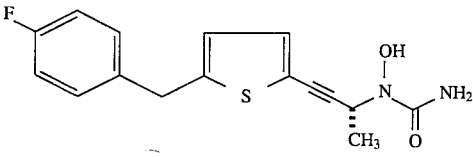

comprising coupling an intermediate compound of the structure

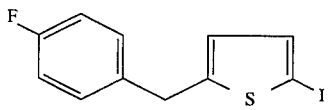

with an intermediate of the structure:

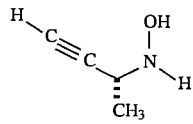

in the presence of a palladium catalyst selected from PdCl₂, Pd(OAc)₂, (CH₃CN)₂PdCl₂, and Pd(PPh₃)₄ followed by reaction of the product thus obtained with an alkali metal isocyanate.
14. The process of claim 13 wherein said palladium catalyst is (CH₃CN)₂PdCl₂.

* * * * *